United States Patent
Marinangeli et al.

(10) Patent No.: US 6,670,516 B1
(45) Date of Patent: Dec. 30, 2003

(54) PROCESS FOR PRODUCING PHENYL-ALKANES USING OLEFIN ISOMERIZATION AND PARAFFIN RECYCLE

(75) Inventors: Richard E. Marinangeli, Arlington Heights, IL (US); Leonid B. Galperin, Wilmette, IL (US); Thomas R. Fritsch, Tucson, AZ (US); R. Joe Lawson, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/327,281

(22) Filed: Dec. 20, 2002

(51) Int. Cl.[7] .............. C07C 2/66; C07C 5/22; C07C 25/107; C07C 5/333
(52) U.S. Cl. .......... 585/323; 585/319; 585/448; 585/455; 585/660; 585/661; 585/740; 585/750; 585/751
(58) Field of Search .................. 585/448, 455, 585/740, 750, 751, 661, 660, 323, 314

(56) References Cited

U.S. PATENT DOCUMENTS

| 5,082,956 A | 1/1992 | Monnier et al. ............ 549/507 |
| 5,196,625 A | 3/1993 | Threlkel et al. ............ 585/513 |
| 5,276,231 A | 1/1994 | Kocal et al. ................. 585/323 |
| 5,510,306 A | 4/1996 | Murray ......................... 502/64 |
| 5,741,759 A | 4/1998 | Gee et al. .................... 507/103 |
| 6,111,158 A | 8/2000 | Marinangeli et al. ........ 585/467 |
| 6,187,981 B1 | 2/2001 | Marinangeli et al. ........ 585/323 |
| 6,323,384 B1 | 11/2001 | Powers et al. ............... 585/671 |

FOREIGN PATENT DOCUMENTS

| WO | WO 99/05082 | 2/1999 | ............. C07C/5/27 |

Primary Examiner—Thuan D. Dang
(74) Attorney, Agent, or Firm—John G. Tolomei; Michael A. Moore

(57) ABSTRACT

A process for producing phenyl-alkanes by paraffin dehydrogenation followed by olefin isomerization and then by alkylation of a phenyl compound by a lightly branched olefin is disclosed. An effluent of the alkylation section comprises paraffins that are recycled to the dehydrogenation step. A process that sulfonates phenyl-alkanes having lightly branched aliphatic alkyl groups to produce modified alkylbenzene sulfonates is also disclosed. In addition, the compositions produced by these processes, which can comprise detergents, lubricants, and lubricant additives, are disclosed.

19 Claims, 1 Drawing Sheet

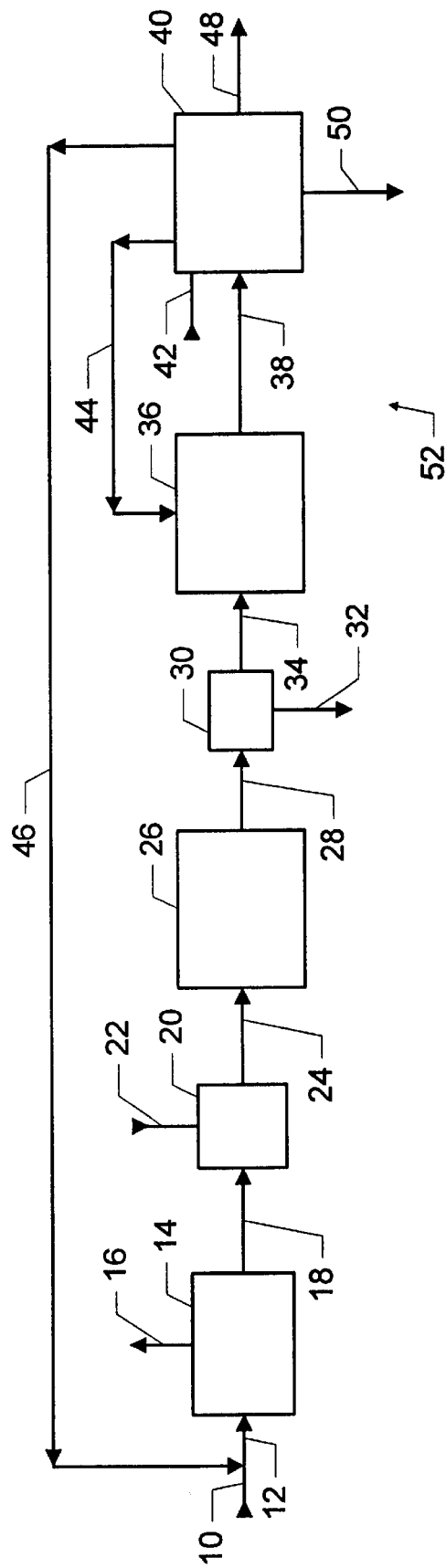

PROCESS FOR PRODUCING PHENYL-ALKANES USING OLEFIN ISOMERIZATION AND PARAFFIN RECYCLE

FIELD OF THE INVENTION

The invention relates generally to the alkylation of phenyl compounds with olefins using solid catalyst, and more specifically to a process for selectively producing particular phenyl-alkanes using a solid alkylation catalyst.

BACKGROUND OF THE INVENTION

More than about thirty years ago, many household laundry detergents were made of branched alkylbenzene sulfonates (BABS). BABS are manufactured from a type of alkylbenzenes called branched alkylbenzenes (BAB). Alkylbenzenes (phenyl-alkanes), refer to a general category of compounds having an aliphatic alkyl group bound to a phenyl group and having the general formula of $(m_i\text{-alkyl}_i)_i$-n-phenyl-alkane. The aliphatic alkyl group consists of an aliphatic alkyl chain, which is referred to by "alkane" in the $(m_i\text{-alkyl}_i)_i$-n-phenyl-alkane formula. Of the chains of the aliphatic alkyl group, the aliphatic alkyl chain is the longest straight chain that has a carbon bound to the phenyl group. The aliphatic alkyl group may also consist of one or more alkyl group branches, each of which is attached to the aliphatic alkyl chain and is designated by a corresponding "$(m_i\text{-alkyl}_i)_i$" in the $(m_i\text{-alkyl}_i)_i$-n-phenyl-alkane formula. If it is possible to select two or more chains of equal lengths as the aliphatic alkyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $m_i$ of the aliphatic alkyl chain. The phenyl group is attached to the aliphatic alkyl group, specifically to carbon number n of the aliphatic alkyl chain. The aliphatic alkylation chain is numbered from one end to the other, the direction being chosen so as to give the lowest number possible to the position of the phenyl group.

The characteristics of BAB are described in U.S. Pat. No. 6,187,981 B1, which is hereby incorporated herein by reference, and therefore it is not necessary to describe them in detail here. Briefly, BAB has a relatively large number of primary carbon atoms per aliphatic alkyl group, the phenyl group in BAB can be attached to any non-primary carbon atom of the aliphatic alkyl chain, and there is a relatively high probability that one of the carbons of the aliphatic alkyl group of BAB is a quaternary carbon.

It is helpful for what follows to briefly describe phenyl-alkanes having quaternary carbon atoms. When a carbon atom on the alkyl side chain not only is attached to two other carbons on the alkyl side chain and to a carbon atom of an alkyl group branch but also is attached to a carbon atom of the phenyl group, the resulting alkyl-phenyl-alkane is referred to as a "quaternary alkyl-phenyl-alkane" or simply a "quat." Thus, quats comprise alkyl-phenyl-alkanes having the general formula m-alkyl-m-phenyl-alkane. If the quaternary carbon is the second carbon atom numbered from an end of the alkyl side chain, the resulting 2-alkyl-2-phenyl-alkane is referred to as an "end quat." If the quaternary carbon is any other carbon atom of the alkyl side chain, then the resulting alkyl-phenyl-alkane is referred to as an "internal quat."

About thirty years ago it became apparent that household laundry detergents made of BABS were gradually polluting rivers and lakes. Investigation into the problem led to the recognition that BABS were slow to biodegrade. Solution of the problem led to the manufacture of detergents made of linear alkylbenzene sulfonates (LABS), which were found to biodegrade more rapidly than BABS. Today, detergents made of LABS are manufactured world-wide. LABS are manufactured from another type of alkylbenzenes called linear alkylbenzenes (LAB). LAB is also described in U.S. Pat. No. 6,187,981 B1. LAB has a linear aliphatic alkyl group with two primary carbon atoms, and the phenyl group in LAB is usually attached to any secondary carbon atom of the linear aliphatic alkyl group.

Over the last few years, other research has identified certain modified alkylbenzene sulfonates, which are referred to herein as MABS. MABS are different in composition from BABS and LABS. MABS also differ from these other alkylbenzene sulfonates by having improved laundry cleaning performance, hard surface cleaning performance, and excellent efficiency in hard water, while also having biodegradability comparable to that of LABS. MABS can be produced by sulfonating modified alkylbenzenes (MAB). MAB is a phenyl-alkane comprising a lightly branched aliphatic alkyl group and a phenyl group and has the general formula $(m_i\text{-alkyl}_i)_i$-n-phenyl-alkane. MAB usually has two, three, or four primary carbons, contains a high proportion of 2-phenyl-alkanes, and has a relatively low proportion of internal quats. MAB is described in detail in U.S. Pat. No. 6,187,981 B1, which discloses an MAB alkylation process. For other alkylation processes and adsorptive separation processes that produce uniquely lightly branched or delinearized alkylbenzenes, see PCT International Publication Nos. WO 99/05082, WO 99/05084, 99/05241, WO 99/05243, and WO99/07656, which are hereby incorporated herein by reference.

Because of the advantages of MABS over other alkylbenzene sulfonates, catalysts and processes are sought that selectively produce MAB with a desired selectivity to 2-phenyl-alkanes and to internal quaternary phenyl-alkanes.

SUMMARY OF THE INVENTION

A process for the production of phenyl-alkanes, in particular modified alkylbenzenes (MAB), by the steps of paraffin dehydrogenation, olefin isomerization, and alkylation of a phenyl compound, in which paraffins in the alkylation effluent are recycled to the dehydrogenation step, is disclosed. The paraffins that are recycled may be linear or nonlinear paraffins, including lightly branched paraffins. Because the recycled paraffins can be converted into lightly branched olefins, this process efficiently recovers paraffins in the alkylation effluent and uses them to produce valuable phenyl-alkane products. This process thus increases the yield of valuable products for a given amount of paraffinic feedstock charged to the process while avoiding the difficulty of separating the paraffins from the monoolefins after the paraffin dehydrogenation step and prior to the alkylation step.

This process, when used for detergent alkylation, produces detergents that meet the increasingly stringent requirements of 2-phenyl-alkanes selectivity and internal quaternary phenyl-alkane selectivity for the production of modified alkylbenzenes (MAB). Thus, the MAB in turn can be sulfonated to produce modified linear alkylbenzene sulfonates (MABS), which have improved cleaning effectiveness in hard and/or cold water while also having biodegradability comparable to that of linear alkylbenzene sulfonates.

It is believed that the MAB and MABS produced by the processes disclosed herein are not necessarily the products that would be produced by the prior art processes that do not recycle paraffins. Without being bound to any particular theory, it is believed that in the dehydrogenation zone the extent of conversion of branched paraffins can be greater than that of normal (linear) paraffins, and/or that the extent of conversion of heavier paraffins can be greater than that of lighter paraffins. In this case, since the extent of conversion of paraffins is limited by equilibrium, the dehydrogenation zone effluent can contain more linear and/or lighter paraffins. Thus, the concentration of linear paraffins and/or lighter paraffins in the recycle paraffin stream could increase. This, in turn, could increase the concentration and ultimately the conversion of linear and/or lighter paraffins in the dehydrogenation zone until the rate of removal from the process of linear and/or lighter paraffins via dehydrogenation and subsequent alkylation equals the rate of introduction into the dehydrogenation zone of those paraffins from the paraffin feedstock and the recycle paraffin stream. Accordingly, for a given extent of olefin conversion in the alkylation zone, the aliphatic alkyl chain of the MAB product of the present invention will be more similar in carbon number to the paraffinic feedstock than that of the prior art processes. The distribution of the number of carbon atoms in the aliphatic alkyl groups of the MAB product of the prior art processes will be skewed to higher carbon numbers compared to that of the present invention. On sulfonation, the MABS product of the present invention will likewise tend to have a carbon number distribution of the aliphatic alkyl chain that is more similar to the paraffinic feedstock than that of the prior art processes. Thus, for a given combination of feedstocks, the processes of this invention could produce particular MAB and MABS products having aliphatic alkyl chain with specially tailored extents of branching that are not necessarily the same as those of the prior art processes.

Additional aspects and embodiments are described in the following description of this invention.

INFORMATION DISCLOSURE

LAB processes are described in the book edited by Robert A. Meyers entitled *Handbook of Petroleum Refining Processes,* (McGraw-Hill, New York, Second Edition, 1997) at pages 1.53 to 1.66, the teachings of which are hereby incorporated herein by reference. Paraffin dehydrogenation processes are described in the Meyers book at pages 5.11 to 5.19, the teachings of which are hereby incorporated herein by reference.

PCT International Publication Nos. WO 99/05082 discloses a process for producing uniquely lightly branched or delinearized alkylbenzenes using olefin isomerization and alkylation, and is incorporated herein by reference.

U.S. Pat. No. 6,111,158 discloses a process for producing MAB by isomerizing olefins and alkylating benzene with the isomerized olefins in the presence of NU-87 zeolite. The teachings of U.S. Pat. No. 6,111,158 are hereby incorporated herein by reference.

U.S. Pat. No. 6,187,981 B1 discloses a process for producing MAB by paraffin isomerization, paraffin dehydrogenation, and alkylation, with paraffin recycle, and is incorporated herein by reference.

U.S. Pat. No. 5,276,231 (Kocal et al.) describes a process for making LAB with selective removal of aromatic by-products of the paraffin dehydrogenation zone of the process. U.S. Pat. No. 5,276,231 discloses recycling paraffins to the dehydrogenation zone, selective hydrogenation of any monoolefins in the paraffin recycle stream, and selective hydrogenation of diolefinic by-products from the dehydrogenation zone. The teachings of U.S. Pat. No. 5,276,231, are hereby incorporated herein by reference.

U.S. Pat. No. 5,196,625 (Threlkel et al.) describes a dimerization process for producing linear and/or mono-branched C10 to C28 olefins that are used for the production of alkylbenzenes and alkylbenzene sulfonates.

Catalysts and conditions for skeletal isomerization of the olefins are disclosed in U.S. Pat. No. 5,510,306 (Murray), U.S. Pat. No. 5,082,956 (Monnier et al.), U.S. Pat. No. 5,741,759 (Gee et al.), and U.S. Pat. No. 6,323,384 B1 (Powers et al.)

DETAILED DESCRIPTION OF THE INVENTION

Two feedstocks consumed in the subject process are a paraffinic compound and a phenyl compound. The paraffinic feedstock may comprise nonbranched (linear) or normal paraffin molecules having a total number of carbon atoms per paraffin molecule of from about 8 to about 28, and in other embodiments from 8 to 15, from 10 to 15, and from 11 to 13 carbon atoms. Two carbon atoms per nonbranched paraffin molecule are primary carbon atoms and the remaining carbon atoms are secondary carbon atoms. A secondary carbon atom is a carbon atom which, although possibly bonded also to other atoms besides carbon, is bonded to only two carbon atoms.

In addition to nonbranched paraffins, other acyclic compounds may be charged to the subject process. These other acyclic compounds may be charged to the subject process either in the paraffinic feedstock containing nonbranched paraffins, or via one or more other streams that are charged to the subject process. One such acyclic compound is a lightly branched paraffin, which as used herein, refers to a paraffin having a total number of carbon atoms of from about 8 to about 28, of which three or four of the carbon atoms are primary carbon atoms and none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms. The lightly branched paraffin may have a total number of from 8 to 15 carbon atoms, and in another embodiment from 10 to 15 carbon atoms, and in yet another embodiment from 11 to 13 carbon atoms. The lightly branched paraffin generally comprises an aliphatic alkane having the general formula of $(p_i\text{-alkyl}_i)_i$-alkane. The lightly branched paraffin consists of an aliphatic alkyl chain, which is referred to by "alkane" in the $(p_i\text{-alkyl}_i)_i$-alkane formula, and is the longest straight chain of the lightly branched paraffin. The lightly branched paraffin also consists of one or more alkyl group branches, each of which is attached to the aliphatic alkyl chain and is designated by a corresponding "$(p_i\text{-alkyl}_i)$" in the $(p_i\text{-alkyl}_i)_i$-alkane formula. If it is possible to select two or more chains of equal lengths as the aliphatic alkyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $p_i$ of the aliphatic alkyl chain. The aliphatic alkyl chain is numbered from one end to the other, the direction being chosen so as to give the lowest numbers possible to the carbon atoms having alkyl group branches.

The alkyl group branch or branches of the lightly branched paraffin may be selected from methyl, ethyl, and propyl groups, with shorter and normal branches being preferred. The lightly branched paraffin may have only one alkyl group branch, but two alkyl group branches are also possible. Lightly branched paraffins having either two alkyl group branches or four primary carbon atoms may comprise less than 40 mol-%, and in another embodiment less than about 25 mol-%, of the total lightly branched paraffins. Lightly branched paraffins having either one alkyl group branch or three primary carbon atoms may comprise more than 70 mol-% of the total lightly branched monoolefins. Any alkyl group branch can be bonded to any carbon on the aliphatic alkyl chain.

Other acyclic compounds that may be charged to the subject process are paraffins that are more highly branched than the lightly branched paraffins. However, on dehydrogenation such highly branched paraffins tend to form highly branched monoolefins which on alkylation tend to form BAB. For example, paraffin molecules consisting of at least one quaternary carbon atom tend on dehydrogenation followed by alkylation to form phenyl-alkanes that have in the aliphatic alkyl portion a quaternary carbon atom that is not bonded by a carbon-carbon bond with a carbon atom of the phenyl portion. Therefore, the quantity of these highly branched paraffins charged to the process is preferably minimized. Paraffin molecules containing at least one quaternary carbon atom comprise, in four embodiments of this invention, less than 10 mol-%, less than 5 mol-%, less than 2 mol-%, and less than 1 mol-% of the paraffinic feedstock or of the sum of all the paraffins that are charged to the subject process.

The paraffinic feedstock is normally a mixture of linear and lightly branched paraffins having different carbon numbers. The production of the paraffinic feedstock is not an essential element of this invention, and any suitable method for producing the paraffinic feedstock may be used. One method for the production of the paraffinic feedstock is the separation of nonbranched (linear) hydrocarbons or lightly branched hydrocarbons from a kerosene boiling range petroleum fraction. Several known processes that accomplish such a separation are known. One process, the UOP Molex™ process, is an established, commercially proven method for the liquid-phase adsorption separation of normal paraffins from isoparaffins and cycloparaffins using the UOP Sorbex separation technology. See Chapters 10.3 and 10.7 in the book entitled *Handbook of Petroleum Refining Process*, Second Edition, edited by Robert A. Meyers, published by McGraw-Hill, New York, 1997. Another suitable, established, and proven process is the UOP Kerosene Isosiv™ Process, which employs vapor-phase adsorption for separating normal paraffins from nonnormal paraffins using molecular sieves in an adsorber vessel. See Chapter 10.6 in the above-mentioned Meyers book. Another vapor-phase adsorption process, which uses ammonia as the desorbent, is described in the paper entitled "Exxon Chemical's Normal Paraffins Technologies," written by R. A. Britton, which was prepared for presentation at the AIChE Annual 1991 National Meeting, Design of Adsorption Systems Session, Los Angeles, Calif., Nov. 21, 1991, and in the article written by W. J. Asher et al. and starting at page 134 of Hydrocarbon Processing, Vol. 48, No. 1 (January 1969). Chapter 11 of the book entitled *Principles of Adsorption and Adsorption Processes*, by Douglas M. Ruthven, published by John Wiley and Sons, New York, 1984, describes other adsorption separation processes. The feed streams to these above-mentioned separation processes, which comprise branched paraffins that are more highly branched than the lightly branched paraffins, can be obtained by extraction or by suitable oligomerization processes. However, the above-mentioned adsorption separation processes are not necessarily equivalent in terms of acceptable concentrations of impurities such as sulfur in their respective feed streams.

The composition of a mixture of linear, lightly branched, and branched paraffins, such as that of the paraffinic feedstock or of the feed stream to the above-mentioned adsorption separation processes, can be determined by analytical methods that are well-known to a person of ordinary skill in the art of gas chromatography and need not be described here in detail. The article written by H. Schulz, et al. and published starting at page 315 of the Chromatographia 1, 1968, which is incorporated herein by reference, describes a temperature-programmed gas chromatograph apparatus and method that is suitable for identifying components in complex mixtures of paraffins. A person of ordinary skill in the art can separate and identify the components in a mixture of paraffins using essentially the apparatus and method described in the article by Schulz et al.

The phenyl feedstock comprises a phenyl compound, which is benzene when the process is detergent alkylation. In a more general case, the phenyl compound of the phenyl feedstock may be alkylated or otherwise substituted derivatives or of a higher molecular weight than benzene, including toluene, ethylbenzene, xylene, phenol, naphthalene, etc., but the product of such an alkylation may not be as suitable a detergent precursor as alkylated benzenes.

For purposes of discussion, the subject process may be divided into a dehydrogenation section, an isomerization section, and an alkylation section. The dehydrogenation section may be configured substantially in the manner described in U.S. Pat. No. 6,187,981 B1, and therefore it is not necessary to describe the dehydrogenation section in detail herein. This invention as set forth in the claims is not limited to any one particular flow scheme for the dehydrogenation section, and suitable flow schemes include but are not limited to those described in U.S. Pat. No. 6,187,981. Any suitable dehydrogenation catalyst may be used, and the particular dehydrogenation catalyst chosen is not critical to the success of this invention. The catalyst may be a layered composition comprising an inner core and an outer layer bonded to the inner core, where the outer layer comprises a refractory inorganic oxide having uniformly dispersed thereon at least one platinum group (Group VIII (IUPAC 8-10)) metal and at least one promoter metal, and where at least one modifier metal is dispersed on the catalyst composition. The outer layer is bonded to the inner core to the extent that the attrition loss can be less than 10 wt-% based on the weight of the outer layer. Such a catalyst composition is described in U.S. Pat. No. 6,177,381, which is hereby incorporated herein by reference. The dehydrogenation conditions, which include those disclosed in U.S. Pat. No. 6,187,981 B1, are selected to minimize cracking and polyolefin byprducts.

Although paraffin or olefin skeletal isomerization may occur at dehydrogenation conditions, olefin skeletal isomerization in the dehydrogenation section is not a requirement of this invention because olefins are isomerized in the hereinafter-described isomerization section. All other dehydrogenation conditions being the same, the extent of paraffin or olefin skeletal isomerization at dehydrogenation conditions generally decreases as the dehydrogenation temperature decreases, so that skeletal isomerization can be minimized by minimizing the dehydrogenation temperature. By skeletal isomerization of a paraffin or olefin molecule at dehydrogenation conditions, it is meant isomerization that increases the number of primary carbon atoms of the paraffin or olefin molecule. The monoolefin-containing dehydrogenated product stream from the paraffin dehydrogenation section is typically a mixture of unreacted paraffins and olefins that correspond, including skeletally, to the paraffins charged to the dehydrogenation section. In an embodiment, minimal skeletal isomerization of the paraffins and olefins occurs in the dehydrogenation section. By minimal skeletal isomerization it is meant that in one embodiment less than 15 mol-%, and in another embodiment less than 10 mol-%, of the paraffins and olefins undergoes skeletal isomerization. Thus, it is preferred that when most of the feed paraffins are linear (unbranched), most of the olefins are linear (unbranched) olefins.

The linear monoolefins in the dehydrogenation reaction effluent are passed to a skeletal isomerization zone, which decreases the linearity and adjusts the number of primary carbon atoms of the olefin molecules. The skeletal isomerization of the molecule can comprise increasing by 2, or in another embodiment by 1, the number of methyl group branches of the aliphatic chain. Because the total number of carbon atoms of the olefin molecule remains the same, each additional methyl group branch causes a corresponding reduction by one of the number of carbon atoms in the aliphatic chain.

The skeletal isomerization step sufficiently decreases the linearity of the dehydrogenation reaction effluent so that after use in alkylation the phenyl-alkane alkylate meets the requirements for primary carbon atoms, 2-phenyl-alkane selectivity, and internal quaternary phenyl-alkane selectivity. Skeletal isomerization of the starting-material olefins can be accomplished in any manner known in the art or by using any catalyst known in the art. Suitable catalysts include ferrierite, ALPO-31, SAPO-11, SAPO-31, SAPO-41, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MeAPSO-11, MeAPSO-31, MeAPSO-41, MeAPSO-46, ELAPO-11, ELAPO-31, ELAPO-41, ELAPSO-11, ELAPSO-31, ELAPSO-41, laumontite, cancrinite, offretite, hydrogen form of stillbite, magnesium or calcium form of mordenite, and magnesium or calcium form of partheite. Suitable MeAPSO-31 catalysts include MgAPSO-31. Many natural zeolites, such as ferrierite, that have an initially reduced pore size can be converted to forms suitable for olefin skeletal isomerization by removing associated alkali metal or alkaline earth metal by ammonium ion exchange and calcination to produce the substantially hydrogen form, as taught in U.S. Pat. Nos. 4,795,623 and 4,924,027. However, H-form mordenite is not a suitable catalyst for skeletal isomerization of the olefinic starting-material. Catalysts and conditions for skeletal isomerization of the olefinic starting-material are disclosed in U.S. Pat. No. 5,510,306 (Murray), U.S. Pat. No. 5,082,956 (Monnier et al.), and U.S. Pat. No. 5,741,759 (Gee et al.). The skeletal isomerization conditions include conditions under which at least a portion, and in another embodiment all, of the hydrocarbons that contact the skeletal isomerization catalyst contact the skeletal isomerization catalyst in the liquid phase. The isomerization temperature is from about 50 to about 400° C. (122 to 752° F.). Although the isomerization catalyst need not contain a Group VIII (IUPAC 8-10) metal, when the isomerization catalyst does contain such a metal the isomerization conditions include a molar ratio of hydrogen per hydrocarbon of greater than 0.01:1.

The isomerized product stream for the production of MAB contains a lightly branched monoolefin. A lightly branched monoolefin, as used herein, refers to a monoolefin having a total number of carbon atoms of from about 8 to about 28, of which three or four of the carbon atoms are primary carbon atoms and none of the remaining carbon atoms are quaternary carbon atoms. The lightly branched monoolefin may have a total number of from 8 to 15 carbon atoms, and in another embodiment from 10 to 15 carbon atoms, and in still another embodiment from 11 to 13 carbon atoms. The isomerized product stream has a concentration of lightly branched monoolefins of greater than about 25 mol-%.

The lightly branched monoolefin generally comprises an aliphatic alkene having the general formula of $(p_i\text{-alkyl}_i)_i$-q-alkene. The lightly branched monoolefin consists of an aliphatic alkenyl chain, which is referred to by "alkene" in the $(p_i\text{-alkyl}_i)_i$-q-alkene formula, and is the longest straight chain containing the carbon-carbon double bond of the lightly branched monoolefin. The lightly branched monoolefin also consists of one or more alkyl group branches, each of which is attached to the aliphatic alkenyl chain and is designated by a corresponding "$(p_i\text{-alkyl}_i)_i$" in the $(p_i\text{-alkyl}_i)_i$-q-alkene formula. If it is possible to select two or more chains of equal lengths as the aliphatic alkenyl chain, the choice goes to the chain carrying the greatest number of alkyl group branches. The subscript counter "i" thus has a value of from 1 to the number of alkyl group branches, and for each value of i, the corresponding alkyl group branch is attached to carbon number $p_i$ of the aliphatic alkenyl chain. The double bond is between carbon number q and carbon number (q+1) of the aliphatic alkenyl chain. The aliphatic alkenyl chain is numbered from one end to the other, the direction being chosen so as to give the lowest number possible to the carbon atoms bearing the double bond.

The lightly branched monoolefin may be an alpha monoolefin or a vinylidene monoolefin, but is preferably an internal monoolefin. As used herein, the term "alpha olefins" refers to olefins having the chemical formula, R—CH=CH$_2$. The term "internal olefins," as used herein, includes di-substituted internal olefins having the chemical formula R—CH=CH—R; tri-substituted internal olefins having the chemical formula R—C(R)=CH—R; and tetra-substituted olefins having the chemical formula R—C(R)=C(R)—R. The di-substituted internal olefins include beta internal olefins having the chemical formula R—CH=CH—CH$_3$. As used herein, the term "vinylidene olefins" refers to olefins having the chemical formula R—C(R)=CH$_2$. In each of the preceding chemical formulas in this paragraph, R is an alkyl group that may be identical to or different from other alkyl group(s), if any, in each formula. Insofar as permitted by the definition of the term "internal olefin", when the lightly branched monoolefin is an internal monoolefin, any two carbon atoms of the aliphatic alkenyl chain may bear the double bond. Suitable lightly branched monoolefins include octenes, nonenes, decenes, undecenes, dodecenes, tridecenes, tetradecenes, pentadecenes, hexadecenes, heptadecenes, octadecenes, nonadecenes, eicosenes, heneicosenes, docosenes, tricosenes, tetracosenes, pentacosenes, hexacosenes, heptacosenes, and octacosenes.

The alkyl group branch or branches of the lightly branched monoolefin are generally selected from methyl, ethyl, and propyl groups, with shorter and normal branches being preferred. Preferably, the lightly branched monoolefin has only one alkyl group branch, but two alkyl group branches are also possible. Lightly branched monoolefins having either two alkyl group branches or four primary carbon atoms may comprise less than 40 mol-%, and in another embodiment less than about 30 mol-%, of the total lightly branched monoolefins, with the remainder of the lightly branched monoolefins having one alkyl group branch. Lightly branched monoolefins having either one alkyl group branch or three primary carbon atoms comprise in one embodiment more than 70 mol-% of the total lightly branched monoolefins. Any alkyl group branch can be bonded to any carbon on the aliphatic alkenyl chain.

The composition of a mixture of lightly branched monoolefins can be determined by analytical methods that are described in U.S. Pat. No. 6,187,981 and need not be described here in detail.

In addition to the lightly branched monoolefin, other acyclic compounds may contact the alkylation catalyst. These other acyclic compounds may be brought into contact with the catalyst either via the isomerized product stream or via one or more other streams. Other acyclic compounds include nonbranched (linear) olefins and nonolefins, including linear and nonlinear paraffins. Nonbranched (linear) olefins which may contact the zeolite have a total number of carbon atoms per paraffin molecule of from about 8 to about 28 in one embodiment, from 8 to 15 in another embodiment, and from 10 to 14 carbon atoms in a third embodiment. Two carbon atoms per nonbranched olefin molecule are primary carbon atoms and the remaining carbon atoms are secondary carbon atoms. A secondary carbon atom is a carbon atom which, although possibly bonded also to other atoms besides carbon, is bonded to only two carbon atoms. The nonbranched olefin may be an alpha monoolefin but is preferably an internal monoolefin. To the extent allowed by the definition of the term "internal olefin", when the nonbranched monoolefin is an internal monoolefin, any two carbon atoms of the aliphatic alkenyl chain may bear the double bond. When present in the isomerized product stream with the lightly branched monoolefins, the linear olefin content in one embodiment is less than or equal to about 75 mol-% of the total monoolefins in the isomerized product stream, and in another embodiment is less than about 60 mol-% of the total monoolefins in the isomerized product stream.

Because of the possible presence in the isomerized product stream of linear monoolefins, in addition to the lightly branched monoolefins, the bulk isomerized product stream may contain, on average, fewer than 3, or between 3 and 4, primary carbon atoms per monoolefin molecule in the isomerized product stream. Depending on the relative proportions of linear and lightly branched monoolefins, the isomerized product stream, or the sum of all the monoolefins that contact the zeolite, may have from 2.25 to 4 primary carbon atoms per monoolefin molecule.

Linear and/or nonlinear paraffins, if any, which may contact the zeolite, via the isomerized product stream or not, have a total number of carbon atoms per paraffin molecule of from about 8 to about 28 carbon atoms in one embodiment, from 8 to 15 carbon atoms in another embodiment, and from 10 to 14 carbon atoms in yet another embodiment. Such linear and nonlinear paraffins are expected to act as a diluent in the alkylation step and not to materially interfere with the alkylation step. However, the presence of such diluents in the alkylation reactor generally results in higher volumetric flow rates of process streams, and, in order to accommodate these higher flow rates, larger equipment in the alkylation reaction circuit (i.e., larger alkylation reactor and more alkylation catalyst), and larger product recovery facilities may be required. In one embodiment, the isomerized product stream does not contain unacceptable concentrations of impurities or poisons which would cause difficulties in the alkylation step. Some impurities can be removed by well-known steps, such as distillation to remove lower-boiling and higher-boiling undesired materials and selective hydrogenation to convert polyolefins, such as diolefins, to monoolefins. When the product of the alkylation step is a specific phenyl-alkane that results from monoalkylating a phenyl compound with a particular lightly branched olefin, the isomerized product stream in one embodiment contains little, and in another embodiment none, of the dimer of that particular lightly branched olefin.

Monoolefins that are more highly branched than the lightly branched monoolefins may also be present in the isomerized product stream, but because on alkylation such highly branched monoolefins tend to form BAB, preferably their concentration in the isomerized product stream is minimized. For example, the isomerized product stream may contain monoolefin molecules having at least one quaternary carbon atom, which tend on alkylation to form phenyl-alkanes that have in the aliphatic alkyl portion a quaternary carbon atom that is not bonded by a carbon-carbon bond with a carbon atom of the phenyl portion. Therefore, monoolefin molecules having at least one quaternary carbon atom comprise in one embodiment less than 10 mol-%, and in another embodiment less than 1 mol-%, of the isomerized product stream or of the sum of all the monoolefins that contact the catalyst.

The product of the skeletal isomerization step contains the lightly branched monoolefins and may be used as the supply of olefins to the alkylation section. Accordingly, the isomerized product stream may be a mixture largely of unreacted paraffins, linear (unbranched) olefins, and branched monoolefins which typically are in the $C_8$–$C_{28}$ range, although those in the $C_8$–$C_{15}$ range are used in the practice of one embodiment of this invention, and those in the $C_{10}$–$C_{15}$ range are used in another embodiment. About 20 to about 60 mol-% of the total monoolefins in the isomerized product stream are linear (unbranched) olefins. The monoalkyl branched olefins in the isomerized product stream are preferably monomethyl-alkenes. The dialkyl branched olefin content of the isomerized product stream, in three embodiments of this invention, is less than about 30 mol-%, between about 10 mol-% and about 20 mol-%, and less than about 10 mol-%, of the isomerized product stream. The isomerized product stream can be formed from a portion or an aliquot portion of the product of the skeletal isomerization step. An aliquot portion of the product of the skeletal isomerization step is a fraction of the product of the skeletal isomerization step that has essentially the same composition as the product of the skeletal isomerization step.

Besides olefin isomerization, paraffin skeletal isomerization may also take place in the olefin isomerization section. However, paraffin isomerization in the olefin isomerization section is not a requirement of this invention. To the extent that paraffin isomerization does occur, the resulting non-linear paraffins will be present in the isomerized product stream along with normal (linear) paraffins. These non-linear paraffins can pass through the hereinafter described alkylation section and then be recycled to the dehydrogenation section where they are mixed with paraffins from the paraffinic feedstock. In the dehydrogenation section, these recycled, non-linear paraffins may or may not be dehydrogenated to monoolefins. Then, as already-isomerized paraffins or as already-isomerized paraffins-turned-olefins, these compounds re-enter the olefin isomerization section where they can undergo further isomerization. Thus, the isomerized product stream contains a mixture of nonlinear paraffins and nonlinear olefins that may be the result of multiple recirculating passes of paraffins through the dehydrogenation, isomerization, and alkylation sections.

The lightly branched monoolefins in the isomerized product stream are reacted with a phenyl compound. The alkylation takes place in an alkylation section consisting of an alkylation reaction zone and an alkylation separation zone. The alkylation section may be configured substantially in the manner described in U.S. Pat. No. 6,187,981 B1, and therefore it is not necessary to describe the alkylation section and its zones in detail herein. This invention as set forth in the claims is not limited to any one particular flow scheme for the alkylation section, and suitable flow schemes include but are not limited to those described in U.S. Pat. No. 6,187,981. Any suitable alkylation catalyst may be used, and the particular alkylation catalyst chosen is not critical to the success of this invention. Alkylation catalysts comprise zeolites having a zeolite structure type selected from the group consisting of BEA, MOR, MTW, and NES. Such zeolites include mordenite, ZSM-4, ZSM-12, ZSM-20, offretite, gmelinite, beta, NU-87, and gottardiite.

It is believed that under alkylation conditions only minimal skeletal isomerization of the lightly branched monoolefin occurs. As used herein, skeletal isomerization of an olefin under alkylation conditions means isomerization that occurs during alkylation and which changes the number of carbon atoms in the aliphatic alkenyl chain of the olefin, in the aliphatic alkyl chain of the phenyl-alkane product, or in any reaction intermediate that is formed or derived from the lightly branched monoolefin prior to the withdrawal of the phenyl-alkane product from the alkylation conditions. By minimal skeletal isomerization it is meant that in one embodiment less than 15 mol-%, and in another embodiment less than 10 mol-%, of the olefin, the aliphatic alkyl chain, and any reaction intermediate undergoes skeletal isomerization. It is further believed that under alkylation conditions minimal skeletal isomerization occurs for any other olefins and any paraffins in the isomerized product stream. Thus, alkylation in one embodiment occurs in the substantial absence of skeletal isomerization of the lightly branched monoolefin, and the extent of light branching of the lightly branched monoolefin is identical to the extent of light branching in the aliphatic alkyl chain in the phenyl-alkane product molecule. Accordingly, the number of primary carbon atoms in the lightly branched monoolefin is preferably the same as the number of primary carbon atoms per phenyl-alkane molecule. Insofar as an additional methyl group branch does form on the aliphatic alkyl chain of the phenyl-alkane product, the number of primary carbon atoms in the phenyl-alkane product may be slightly higher the number of primary carbon atoms in the lightly branched monoolefin. Finally, although the formation of 1-phenyl-alkane product is not significant at alkylation conditions, insofar as a 1-phenyl-alkane molecule is formed by alkylating a phenyl compound with a lightly branched monoolefin having a primary carbon atom on each end of the aliphatic alkenyl chain, the number of primary carbon atoms in the phenyl-alkane product will be slightly less than the number of primary carbon atoms in the lightly branched monoolefin.

The alkylation of the phenyl compound with the lightly branched monoolefins produces $(m_i$-alkyl$_i)_i$-n-phenyl-alkanes, where the aliphatic alkyl group has two, three, or four primary carbon atoms per phenyl-alkane molecule. In one embodiment, the aliphatic alkyl group has three primary carbon atoms per phenyl-alkane molecule, and in another embodiment one of the three primary carbon atoms is in a methyl group at one end of the aliphatic alkyl chain, the second primary carbon atom is in a methyl group at the other end of the chain, and the third primary carbon atom is in a single methyl group branch attached to the chain. In this embodiment, the alkylation produces monomethyl-phenyl-alkanes. However, it is not necessary that all of the $(m_i$-alkyl$_i)_i$-n-phenyl-alkanes produced have the same number of primary carbon atoms per phenyl-alkane molecule. In one embodiment from about 0 mol-% to about 75 mol-%, and in another embodiment from about 0 mol-% to about 40 mol-%, of the $(m_i$-alkyl$_i)_i$-n-phenyl-alkanes produced may have 2 primary carbon atoms per phenyl-alkane molecule. In one embodiment as many as possible, and in another embodiment from about 25 mol-% to about 100 mol-%, of the $(m_i$-alkyl$_i)_i$-n-phenyl-alkanes produced may have 3 primary carbon atoms per phenyl-alkane molecule. In one embodiment from about 0 mol-% to about 40 mol-% of the $(m_i$-alkyl$_i)_i$-n-phenyl-alkanes produced may have 4 primary carbon atoms. Thus, (m-methyl)-n-phenyl-alkanes having only one methyl group branch are preferred and are referred to herein as monomethyl-phenyl-alkanes. It is expected that the number of primary, secondary, and tertiary carbon atoms per product phenyl-alkane molecule can be determined by high resolution multipulse nuclear magnetic resonance (NMR) spectrum editing and distortionless enhancement by polarization transfer (DEPT), which is described in the brochure entitled "High Resolution Multipulse NMR Spectrum Editing and DEPT," which is distributed by Bruker Instruments, Inc., Manning Park, Billerica, Mass., USA, and which is incorporated herein by reference.

It should be pointed out that, on alkylation of the phenyl compound with the lightly branched monoolefins, the parameters for how selective the alkylation is to 2-phenyl-alkanes and to internal quaternary phenyl-alkanes have been determined in the prior art using two slightly different analytical and computational methods. In particular, U.S. Pat. Nos. 6,111,158 and 6,187,981 (which are incorporated herein by reference) use slightly methods that result in slightly different selectivities. In order to prevent any confusion between these selectivities and for purposes of this patent application, selectivities determined by the methods taught in U.S. Pat. No. 6,111,158 are referred to hereinafter as simplified selectivities, and selectivities determined by the methods taught in U.S. Pat. No. 6,187,981 are referred to herein as selectivities (i.e., without the adjective "simplified"). The alkylation of the phenyl compound with the lightly branched monoolefins has a selectivity of 2-phenyl-alkanes of from about 40 to about 100 in one embodiment and from about 60 to about 100 in another embodiment, and an internal quaternary phenyl-alkane selectivity of less than 10 in one embodiment and less than 5 in another embodiment.

Quaternary phenyl-alkanes can form by alkylating the phenyl compound with a lightly branched monoolefin having at least one tertiary carbon atom. A tertiary carbon atom is a carbon atom which, while also possibly bonded to other atoms besides carbon, is bonded to only three carbon atoms. If, on alkylation, a tertiary carbon atom of the monoolefin forms a carbon-carbon bond with one of the carbon atoms of the phenyl compound, that tertiary carbon atom becomes a quaternary carbon atom of the aliphatic alkyl chain. Depending on the location of the quaternary carbon atom with respect to the ends of the aliphatic alkyl chain, the resulting quaternary phenyl-alkane may be either an internal or an end quat.

At least a portion of the overhead liquid stream of the paraffin column in the alkylation separation zone is recycled to the dehydrogenation section. In one embodiment, the portion of the overhead liquid stream of the paraffin column that is recycled to the dehydrogenation section is an aliquot portion of the overhead liquid stream. The paraffin column overhead stream comprises paraffins having a total number of carbon atoms per paraffin molecule of from about 8 to about 28 carbon atoms in one embodiment, from 8 to 15 carbon atoms in another embodiment, from 10 to 15 carbon atoms in a third embodiment, and 11 to 13 carbon atoms in a fourth embodiment.

Some of the paraffin column overhead liquid stream may also be recycled to the isomerization section, since the paraffin column overhead liquid stream may contain monoolefins because olefin conversion in alkylation is not 100%. However, the concentration of monoolefins in the paraffin column overhead liquid stream is generally less than 0.3 wt-%. Monoolefins in the paraffin column overhead liquid stream may be recycled to the isomerization section and/or the dehydrogenation section. The paraffin column overhead liquid stream may also contain paraffins having at least one quaternary carbon atom, but preferably the concentration of such paraffins is minimized.

Several variants of the process disclosed herein are possible. One variant includes the selective hydrogenation of diolefins that may be present in the dehydrogenated product stream, since diolefins may be formed during the catalytic dehydrogenation of paraffins. Another variant of the process includes selective removal of aromatic by-products that may be present in the dehydrogenated product stream. The aromatic by-products may be selectively removed from the isomerized product stream, the dehydrogenated product steam, the overhead liquid stream of the paraffin column that is recycled to the dehydrogenation section, or the selective diolefin hydrogenation product stream (if any). Information on selective diolefin hydrogenation and selective removal of aromatic by-products is disclosed in U.S. Pat. No. 6,187,981 and the references cited therein.

In one embodiment, the process produces an MAB composition comprising phenyl-alkanes having one phenyl group and one aliphatic alkyl group, wherein the phenyl-alkanes have:

(i) an average weight of the aliphatic alkyl groups of the phenyl-alkanes of between the weight of a $C_{10}$ aliphatic alkyl group and a $C_{13}$ aliphatic alkyl group;

(ii) a content of phenyl-alkanes having the phenyl group attached to the 2- and/or 3-position of the aliphatic alkyl group of greater than 55 wt-% of the phenyl-alkanes; and (iii) an average level of branching of the aliphatic alkyl groups of the phenyl-alkanes of from 0.25 to 1.4 alkyl group branches per phenyl-alkane molecule when the sum of the contents of 2-phenyl-alkanes and 3-phenyl-alkanes is more than 55 wt-% and less than or equal to 85 wt-% of the phenyl-alkanes, or an average level of branching of the aliphatic alkyl groups of the phenyl-alkanes of from 0.4 to 2.0 alkyl group branches per phenyl-alkane molecule when the sum of the concentrations of 2-phenyl-alkanes and the 3-phenyl-alkanes is greater than 85 wt-% of the phenyl-alkanes; and (iv) wherein the aliphatic alkyl groups of the phenyl-alkanes comprise primarily linear aliphatic alkyl groups, mono-branched aliphatic alkyl groups, or di-branched aliphatic alkyl groups, and wherein the alkyl group branches if any on the aliphatic alkyl chain of the aliphatic alkyl groups comprise primarily small substituents, such as methyl group branches, ethyl group branches, or propyl group branches, and wherein the alkyl group branches if any attach to any position on the aliphatic alkyl chain of the aliphatic alkyl groups provided that phenyl-alkanes having at least one quaternary carbon atom on the aliphatic alkyl group comprise less than 20% of the phenyl-alkanes.

One process for producing this MAB composition comprises first dehydrogenating paraffins to produce the corresponding monoolefins. The process comprises isomerizing monoolefins having an average weight between the weight of a $C_{10}$ paraffin and a $C_{13}$ paraffin to produce isomerized monoolefins having an average level of branching of from 0.25 to 1.4, or of from 0.4 to 2.0, alkyl group branches per olefin molecule. These isomerized monoolefins primarily comprise linear monoolefins, mono-branched monoolefins, or di-branched monoolefins, and the alkyl group branches if any on the aliphatic alkyl chain of the isomerized monoolefins primarily comprise small substituents, such as methyl group branches, ethyl group branches, or propyl group branches. The alkyl group branches of the isomerized monoolefins may be attached to any position on the aliphatic alkyl chain of the olefin, subject to certain limitations that depend on the desired characteristics of the resultant phenyl-alkanes. The isomerized monoolefins alkylate a phenyl compound to produce phenyl-alkanes. The resultant phenyl-alkanes have the characteristics that the phenyl-alkanes having the phenyl group attached to the 2- and/or 3-position of the aliphatic alkyl group comprise greater than 55 wt-% of the phenyl-alkanes, and the phenyl-alkanes having at least one quaternary carbon atom on the aliphatic alkyl group comprise less than 20% of the phenyl-alkanes.

Sulfonation of the phenyl-alkanes produced by the processes of this invention and neutralization of the sulfonated product can be accomplished by the methods described in U.S. Pat. No. 6,187,981.

In other aspects of the present invention, this invention is the MAB compositions and the MABS compositions produced by the processes disclosed herein. The MAB compositions produced by the processes of this invention may comprise lubricants, and the MABS compositions produced by the processes of this invention may comprise lubricant additives.

A complete operation of the process aspect of this invention can be more fully understood from a process flow for an embodiment of this invention. The drawing shows an arrangement for an integrated dehydrogenation-isomerization-alkylation scheme of this invention. The following description of the drawing is not meant to preclude other arrangements for the process flow of this invention and is not intended to limit this invention as set forth in the claims.

Referring now to the drawing, a paraffinic feedstock comprising $C_{10}$–$C_{13}$ normal paraffins enters the process through line 10. The paraffinic feedstock combines with a paraffinic recycle stream comprising $C_{10}$–$C_{13}$ normal paraffins flowing in line 46 to form a combined feed stream flowing in line 12. The combined feed stream enters dehydrogenation section 14 where the paraffins are dehydrogenated to olefins. Hydrogen, a byproduct of the dehydrogenation reactions, is vented from the process through line 16. The dehydrogenated product stream in line 18 contains $C_{10}$–$C_{13}$ normal paraffins, $C_{10}$–$C_{13}$ normal monoolefins, $C_{10}$–$C_{13}$ normal diolefins, and aromatic byproducts. In the selective hydrogenation section 20, the diolefins in the dehydrogenated product stream are selectively hydrogenated to monoolefins. Makeup hydrogen enters section 20 through line 22. The selective hydrogenation product stream, which contains $C_{10}$–$C_{13}$ normal paraffins, $C_{10}$–$C_{13}$ normal monoolefins, and aromatic byproducts, flows through line 24 to olefin isomerization section 26. In section 26, the normal monoolefins are isomerized to lightly branched monoolefins. The isomerized product stream in line 28 contains $C_{10}$–$C_{13}$ lightly branched monoolefins, $C_{10}$–$C_{13}$ normal paraffins, and aromatic byproducts. The aromatic byproducts are removed in aromatics removal section 30 and are rejected from the process via line 32. The aromatics removal section product stream, which contains $C_{10}$–$C_{13}$ lightly branched monoolefins and $C_{10}$–$C_{13}$ normal paraffins, flows through line 34 to the alkylation section generally denoted 52. The alkylation section 52 comprises an alkylation reaction zone 36 and an alkylation separation zone 40. Both the aromatics removal section product stream and a benzene-containing phenyl recycle stream in line 44 are charged to alkylation reaction zone 36, where the $C_{10}$–$C_{13}$ lightly branched monoolefins alkylate benzene to produce MAB. The alkylation reaction zone effluent stream contains benzene, $C_{10}$–$C_{13}$ normal paraffin, MAB, as well as heavy alkylbenzenes such as byproduct polyalkylbenzenes. This effluent stream flows through line 38 to the alkylation separation zone 40. A phenyl feedstock comprising benzene and flowing in line 42 is also introduced to the alkylation separation zone 40. Four streams are recovered from alkylation separation zone 40. One of the four streams is the phenyl recycle stream flowing in line 44 and another is the paraffinic recycle stream in line 46. Heavy alkylbenzenes are recovered from zone 40 and rejected from the process through line 50. Lastly, line 48 carries the alkylation section product stream comprising MAB.

All references herein to groups of elements are to the Periodic Table of the Elements, "CRC Handbook of Chemistry and Physics," CRC Press, Boca Raton, Fla., 80$^{th}$ Edition, 1999–2000.

The following examples are solely for purposes of illustration and are not meant to limit the scope of this invention to the embodiments shown in the examples.

EXAMPLE 1

A 100 cc sample of a catalyst comprising 50 wt-% MgAPSO-31 bound with gamma alumina was placed in a reactor tube having an inside diameter of 2.22 cm (⅞ in). A feed consisting of a mixture of 1-dodecene was passed over the catalyst at a liquid hourly space velocity of 5 hr$^{-1}$. The catalyst temperature was initially set to 250° C. (482° F.) and then adjusted to maintain a desired conversion of linear olefins.

The product was analyzed by gas chromatography. A Hewlett Packard (HP) gas chromatograph HP5890 equipped with a split/splitless injector and flame ionization detector (FID) was used. The gas chromatograph was equipped with a hydrogenator insert tube in the injector. The column was a 50-meter Hewlett Packard HP PONA column having an inside diameter of 0.2 mm. An 11 mm Restek red lite septa and an HP O-ring for the inlet liner were used. The gas chromatographic parameters included: hydrogen carrier gas; 138 kPa(g) (20 psi(g)) column head pressure; 1 ml/min column flow; 250 ml/min split vent; 4 ml/min septum purge; 0.2 microliter injection volume; 175° C. (367° F.) injector temperature; 275° C. (527° F.) detector temperature; and an oven temperature program consisting of a hold at 50° C. (122° F.) for 5 min, a ramp at 3° C./min (5° F./min) to 175° C. (347° F.), and a ramp at 10° C./min (18° F./min) to 270° C. (518° F.). A sample was made ready for injection by weighing 4–5 mg of the sample into a 2 ml gas chromatograph auto sampler vial. The catalyst for the hydrogenator was prepared by preparing a solution of 20 g nickel nitrate hexahydrate and 40 ml methanol. The nickel nitrate solution was slowly poured over 20 g "Chromosorb P", which is a calcined diatomite made from crushed firebrick, in an evaporating dish. The mixture in the evaporating dish was warmed with constant stirring to 65° C. (149° F.) on a hot plate to evaporate the methanol until the mixture appeared dry. A weight of 3 g of the mixture was then placed into the hydrogenator insert tube and held in position with glass wool at each end. To activate the catalyst, hydrogen carrier gas was passed at 60 ml/min through the catalyst and the temperature was raised to 350° C. (662° F.), and the catalyst was treated at these conditions for 3 hours. Standards required for this method are n-decane, n-undecane, n-dodecane, n-tridecane, and n-tetradecane. Relative positions of the mono methyl isomers are given in the previously mentioned article by H. Schultz et al.

The products were summed into five classifications as follows, with each classification's sum denoted as shown in brackets: light products with carbon numbers of 11 or lower [$C_{11}$-], linear olefins [linears], monomethyl branched olefins [mono], dimethyl and ethyl branched olefins [di], and heavy products with carbon numbers of $C_{13}$ or higher [$C_{13}$+]. Also, the following performance measures were calculated:

Conversion=100*(1−([linears]$_{product}$/[linears]$_{feed}$))

Monomethyl=100*([mono]/([mono]+[di]))

Lights=100*([$C_{11}$-]/([$C_{11}$-]+[linears]+[mono]+[di]+[$C_{13}$+]))

Heavies=100*([$C_{13}$+]/([$C_{11}$-]+[linears]+[mono]+[di]+[$C_{13}$+]))

The results are shown in Table 1:

TABLE 1

| Results | | | |
|---|---|---|---|
| Conversion | Monomethyl | Lights | Heavies |
| 69.9 | 86.8 | 0.64 | 3.53 |

EXAMPLE 2

Example 1 was repeated, except that the feed consisted of a blend of $C_{11}$, $C_{12}$, and $C_{13}$ linear olefins. The feed contained 28.7 mol-% $C_{11}$, 39.6 mol-% $C_{12}$, and 31.7 mol-% $C_{13}$. The product contained monomethyl branched olefins. The distribution of monomethyl branched olefins in the product was 30.9 mol-% $C_{11}$, 42.4 mol-% $C_{12}$, and 26.7 mol-% $C_{13}$. This example shows that without recycling the distribution of the number of carbon atoms of the monomethyl branched olefin product is different from the distribution of carbon atoms of the feed.

EXAMPLE 3

This example is prophetic. A process is operated as shown in the drawing except without a paraffin recycle stream flowing in line 46. A paraffinic feedstock enters the process through line 10 and MAB is recovered in line 48, and the process operates at steady state conditions. The stream flowing in line 24 has the composition of the feed in Example 2, and the stream flowing in line 28 has the composition of the product in Example 2. Then the flow of a paraffin recycle stream in line 46 is started. Once steady state conditions are reestablished, the distribution of the number of carbon atoms of the aliphatic alkyl groups of the MAB product is skewed to lower carbon numbers than that which is obtained when the process is operated without a paraffin recycle stream.

EXAMPLE 4

This example is prophetic. A process is operated as shown in the drawing. A paraffinic feedstock enters the process through line 10 and MAB is recovered in line 48, and the process operates at steady state conditions. The stream flowing in line 28 has the composition shown in Table 1.

EXAMPLE 5

A starting-material of 1-dodecene was isomerized to produce an isomerized product stream comprising a blend of monomethyl $C_{12}$ olefins and having the composition shown in Table 2.

TABLE 2

Composition of Isomerized Product Stream

| Olefin Component | Content (wt-%) |
|---|---|
| Lights[1] | 0.64 |
| Linear olefins[2] | 30.11 |
| 6-methyl undecene | 7.66 |
| 5-methyl undecene | 15.33 |
| 4-methyl undecene | 11.82 |
| 3-methyl undecene | 12.95 |
| 2-methyl undecene | 8.87 |
| Other alkyl olefins[3] | 9.05 |
| Heavies[4] | 3.53 |
| Total | 99.96 |

[1]Lights include olefins having fewer than 12 carbon atoms.
[2]Linear olefins include $C_{12}$ linear olefins.
[3]Other alkyl olefins include dimethyl, trimethyl, and other $C_{12}$ olefins
[4]Heavies include $C_{12}$ olefin dimers and trimers.

The isomerized product stream was mixed with benzene to produce a combined feedstock consisting of 93.3 wt-% benzene and 6.7 wt-% isomerized product stream, which corresponds to a molar ratio of benzene per olefin of about 30:1. A cylindrical reactor, which has a inside diameter of 0.875 in (22.2 mm), was loaded with 75 cc (53.0 g.) of extrudate prepared in Example 1 of U.S. Pat. No. 6,111,158.

The combined feedstock was passed to the reactor and contacted the extrudate at a LHSV of 2.0 hr$^{-1}$, a total pressure of 500 psi(g) (3447 kPa(g)), and a reactor inlet temperature of 125° C. (257° F.). At these conditions, the reactor lined out over a period of 24 hours and then a first liquid product was collected over the period of the next 6 hours.

After the period of 6 hours of collecting the first liquid product, and with the combined feedstock flowing to the reactor at a LHSV of 2.0 hr$^{-1}$ and a total pressure of 500 psi(g) (3447 kPa(g)), the reactor inlet temperature was increased from 125° C. (257° F.) to 150° C. (302° F.). The reactor lined out over a period of 12 hours with the combined feedstock passing to the reactor and contacting the extrudate at a LHSV of 2.0 hr$^{-1}$, a total pressure of 500 psi(g) (3447 kPa(g)), and a reactor inlet temperature of 150° C. (302° F.). At these conditions, a second liquid product was collected over the period of the next 6 hours. The results for the second liquid product are shown in Table 3.

After the period of 6 hours of collecting the second liquid product, the flow of combined feedstock to the reactor was maintained at a LHSV of 2.0 hr$^{-1}$ and the total pressure was maintained at 500 psi(g) (3447 kPa(g)). At these conditions, the reactor inlet temperature was increased from 150° C. (302° F.) to 175° C. (347° F.). The reactor lined out over a period of 12 hours with the combined feedstock passing to the reactor and contacting the extrudate at a LHSV of 2.0 hr$^{-1}$, a total pressure of 500 psi(g) (3447 kPa(g)), and a reactor inlet temperature of 175° C. (347° F.). At these conditions, a third liquid product was collected over the period of the next 6 hours. The third liquid product was analyzed by $^{13}C$ NMR in the manner previously described. The simplified 2-phenyl-alkane selectivity and simplified internal quaternary phenyl-alkane selectivity for the third liquid product are shown in Table 3. The end quaternary phenyl-alkane selectivities are determined using the analytical and computational methods taught in U.S. Pat. No. 6,187,981.

TABLE 3

Liquid Product Analysis

| Reactor Inlet Temperature ° C. (° F.) | Simplified 2-Phenyl-Alkane Selectivity | Simplified Internal Quaternary Phenyl-Alkane Selectivity |
|---|---|---|
| 150 (302) | 66.4 | 4.6 |
| 175 (347) | 77.7 | 2.9 |

Thus, the alkylation in the example has a 2-phenyl-alkane selectivity of from 40 to 100 and a internal quaternary phenyl-alkane selectivity of less than 10. Although this example did not employ paraffin recycle, it is believed that if paraffin recycle had been used in accord with this invention, then that the 2-phenyl-alkane selectivity would have been from 40 to 100 and the internal quaternary phenyl-alkane selectivity would have been less than 10.

What is claimed is:

1. A process for producing phenyl-alkanes, the process comprising the steps of:

a) dehydrogenating a feedstock comprising $C_8$–$C_{28}$ paraffins in a dehydrogenation section operating at dehydrogenation conditions sufficient to dehydrogenate paraffins, and recovering from the dehydrogenation section a dehydrogenated product stream comprising monoolefins and paraffins;

b) passing at least a portion of the dehydrogenated product stream to an isomerization section operating at isomerization conditions sufficient to isomerize olefins, and recovering from the isomerization section an isomerized product stream comprising monoolefins and paraffins, wherein the monoolefins in the isomerized product stream have from about 8 to about 28 carbon atoms, and wherein at least a portion of the monoolefins in the dehydrogenated product stream have 3 or 4 primary carbon atoms and no quaternary carbon atoms;

c) passing a phenyl compound and at least a portion of the isomerized product stream comprising monoolefins to an alkylation section, operating the alkylation section at alkylation conditions sufficient to alkylate the phenyl compound with monoolefins in the presence of an alkylation catalyst to form phenyl-alkanes comprising molecules having one phenyl portion and one aliphatic alkyl portion containing from about 8 to about 28 carbon atoms; wherein at least a portion of the phenyl-alkanes formed in the alkylation section have 2, 3, or 4 primary carbon atoms and no quaternary carbon atoms except for any quaternary carbon atom bonded by a carbon-carbon bond with a carbon atom of the phenyl portion; and wherein the alkylation has a selectivity to 2-phenyl-alkanes of from 40 to 100 and a selectivity to internal quaternary phenyl-alkanes of less than 10;

d) recovering from the alkylation section an alkylate product stream comprising phenyl-alkanes and a recycle stream comprising paraffins; and e) passing at least a portion of the recycle stream to the dehydrogenation section.

2. The process of claim 1 further characterized in that at least one of the at least a portion of the dehydrogenated product stream and the at least a portion of the isomerized product stream comprises monoolefins having from about 8 to about 28 carbon atoms.

3. The process of claim 2 further characterized in that at least a portion of the monoolefins in at least one of the at least a portion of the dehydrogenated product stream and the at least a portion of the isomerized product stream comprise lightly branched monoolefins.

4. The process of claim 3 further characterized in that the at least a portion of the isomerized product stream has a concentration of lightly branched monoolefins of greater than about 25 mol-% of the at least a portion of the isomerized product stream.

5. The process of claim 2 further characterized in that at least a portion of the monoolefins in at least one of the at least a portion of the isomerized product stream and the at least a portion of the dehydrogenated product stream comprise linear monoolefins.

6. The process of claim 5 further characterized in that the at least a portion of the isomerized product stream has a concentration of linear monoolefins of less than or equal to about 75 mol-% of the at least a portion of the isomerized product stream.

7. The process of claim 2 further characterized in that at least a portion of the monoolefins in at least one of the at least a portion of the dehydrogenated product stream and the at least a portion of the isomerized product stream has at least one quaternary carbon atom.

8. The process of claim 1 further characterized in that the at least a portion of the isomerized product stream has a concentration of olefins having at least one quaternary carbon atom of less than about 10 mol-% of the at least a portion of the isomerized product stream.

9. The process of claim 1 further characterized in that the dehydrogenation section contains a dehydrogenation catalyst comprising at least one Group VIII (IUPAC 8–10) metal, a promoter metal, a modifier metal, and a refractory inorganic oxide, further characterized in that the dehydrogenation catalyst comprises an inner core and an outer layer bonded to the inner core, the outer layer comprising an outer refractory inorganic oxide having uniformly dispersed thereon the at least one Group VIII (IUPAC 8–10) metal and the promoter metal, and the dehydrogenation catalyst further having dispersed thereon the modifier metal.

10. The process of claim 1 further characterized in that the isomerization section contains an isomerization catalyst comprising a support material selected from the group consisting of ferrierite, SAPO-11, and MgAPSO-31.

11. The process of claim 1 further characterized in that the isomerization section operates at isomerization conditions comprising a temperature of from about 50 to about 400° C.

12. The process of claim 1 further characterized in that the isomerization section contains an isomerization catalyst comprising a Group VIII (IUPAC 8–10) metal and that the isomerization section operates at isomerization conditions comprising a molar ratio of hydrogen per hydrocarbon of greater than 0.01:1.

13. The process of claim 1 further characterized in that the alkylation catalyst comprises a zeolite having a zeolite structure type selected from the group consisting of BEA, MOR, MTW, and NES.

14. The process of claim 1 wherein the phenyl compound comprises a compound selected from the group consisting of benzene, toluene, and ethylbenzene.

15. The process of claim 1 wherein the monoolefins comprise monomethyl-alkenes.

16. The process of claim 1 wherein the phenyl-alkanes comprise monomethyl-phenyl-alkanes.

17. The process of claim 1 further characterized in that the at least a portion of the recycle stream has a concentration of monoolefins of less than 0.3 wt-%.

18. The process of claim 1 further characterized in that at least a portion of the alkylate product stream is contacted with a sulfonating agent at sulfonation conditions sufficient to sulfonate phenyl-alkanes and to produce a sulfonated product stream comprising phenyl-alkane sulfonic acids, and at least a portion of the sulfonated product stream is contacted with a neutralizing agent at neutralization conditions sufficient to neutralize phenyl-alkane sulfonic acids and to produce a neutralized product stream comprising phenyl-alkane sulfonates.

19. A process for producing phenyl-alkanes, the process comprising the steps of:
a) passing a feed stream comprising paraffins to a dehydrogenation section, operating the dehydrogenation section at dehydrogenation conditions sufficient to dehydrogenate paraffins, and recovering from the dehydrogenation section a dehydrogenated product stream comprising monoolefins and paraffins;
b) passing at least a portion of the dehydrogenated product stream to an isomerization section, operating the isomerization section at isomerization conditions sufficient to isomerize monoolefins, and recovering from the isomerization section an isomerized product stream comprising monoolefins;
c) passing a phenyl compound and at least a portion of the isomerized product stream comprising monoolefins to an alkylation section, operating the alkylation section at alkylation conditions sufficient to alkylate the phenyl compound with monoolefins in the presence of an alkylation catalyst to form phenyl-alkanes comprising molecules having one phenyl group and one aliphatic alkyl group, wherein the phenyl-alkanes have:
(i) an average weight of the aliphatic alkyl groups of the phenyl-alkanes of between the weight of a $C_{10}$ aliphatic alkyl group and a $C_{13}$ aliphatic alkyl group;
(ii) a content of phenyl-alkanes having the phenyl group attached to the 2- and/or 3-position of the aliphatic alkyl group of greater than 55 wt-% of the phenyl-alkanes; and
(iii) an average level of branching of the aliphatic alkyl groups of the phenyl-alkanes of from 0.25 to 1.4 alkyl group branches per phenyl-alkane molecule when the sum of the contents of 2-phenyl-alkanes and 3-phenyl-alkanes is more than 55 wt-% and less than or equal to 85 wt-% of the phenyl-alkanes, or an average level of branching of the aliphatic alkyl groups of the phenyl-alkanes of from 0.4 to 2.0 alkyl group branches per phenyl-alkane molecule when the sum of the concentrations of 2-phenyl-alkanes and the 3-phenyl-alkanes is greater than 85 wt-% of the phenyl-alkanes; and wherein the aliphatic alkyl groups of the phenyl-alkanes comprise linear aliphatic alkyl groups, mono-branched aliphatic alkyl groups, or di-branched aliphatic alkyl groups, and wherein the alkyl group branches if any on the aliphatic alkyl chain of the aliphatic alkyl groups comprise methyl group branches, ethyl group branches, or propyl group branches, and wherein the alkyl group branches if any attach to any position on the aliphatic alkyl chain of the aliphatic alkyl groups provided that phenyl-alkanes having at least one quaternary carbon atom on the aliphatic alkyl group comprise less than 20% of the phenyl-alkanes;

d) recovering from the alkylation section an alkylate product stream comprising phenyl-alkanes and a recycle stream comprising paraffins; and e) passing at least a portion of the recycle stream to the dehydrogenation section.

* * * * *

UNITED STATES PATENT AND TRADEMARK OFFICE
CERTIFICATE OF CORRECTION

PATENT NO. : 6,670,516 B1 Page 1 of 1
DATED : December 30, 2003
INVENTOR(S) : Richard E. Marinangeli et al.

It is certified that error appears in the above-identified patent and that said Letters Patent is hereby corrected as shown below:

Column 19,
Line 36, the phrase "claim 1" should be replaced with the phrase -- claim 7 --.

Signed and Sealed this

Twenty-third Day of March, 2004

JON W. DUDAS
*Acting Director of the United States Patent and Trademark Office*